(12) United States Patent
Valtchev

(10) Patent No.: US 7,338,432 B2
(45) Date of Patent: Mar. 4, 2008

(54) URETHRAL SLING INTRODUCER AND METHOD OF USE

(76) Inventor: Konstantin Valtchev, 600 Sherbourne St., Suite 507, Toronto, Ontario (CA) M4X 1W4

( * ) Notice: Subject to any disclaimer, the term of this patent is extended or adjusted under 35 U.S.C. 154(b) by 812 days.

(21) Appl. No.: 10/715,238

(22) Filed: Nov. 17, 2003

(65) Prior Publication Data

US 2005/0107660 A1 May 19, 2005

(51) Int. Cl.
*A61F 2/02* (2006.01)
(52) U.S. Cl. ........................................... 600/30
(58) Field of Classification Search ............ 600/29–32, 600/563, 37; 128/897, 898; 606/1
See application file for complete search history.

(56) References Cited

U.S. PATENT DOCUMENTS

| | | | |
|---|---|---|---|
| 4,674,502 A * | 6/1987 | Imonti ........................ | 606/177 |
| 4,911,164 A | 3/1990 | Roth | |
| 5,053,043 A | 10/1991 | Gottesman et al. | |
| 5,232,443 A | 8/1993 | Leach | |
| 5,348,541 A | 9/1994 | Lyell | |
| 5,395,313 A * | 3/1995 | Naves et al. .................. | 604/22 |
| 5,843,113 A | 12/1998 | High | |
| 5,899,909 A | 5/1999 | Claren et al. | |
| 6,030,393 A | 2/2000 | Corlew | |
| 6,273,852 B1 | 8/2001 | Lehe et al. | |
| 6,319,272 B1 | 11/2001 | Brenneman et al. | |
| 6,406,423 B1 | 6/2002 | Scetbon | |
| RE37,815 E * | 8/2002 | Rizvi ......................... | 606/222 |
| 6,475,139 B1 | 11/2002 | Miller | |
| 6,478,727 B2 | 11/2002 | Scetbon | |
| 6,491,703 B1 | 12/2002 | Ulmsten | |
| 6,638,210 B2 * | 10/2003 | Berger ......................... | 600/30 |
| 6,960,160 B2 * | 11/2005 | Browning ..................... | 600/37 |
| 2001/0018549 A1 | 8/2001 | Scetbon | |
| 2002/0143234 A1 * | 10/2002 | LoVuolo ....................... | 600/30 |
| 2003/0036676 A1 | 2/2003 | Scetbon | |

* cited by examiner

*Primary Examiner*—Samuel G Gilbert
(74) *Attorney, Agent, or Firm*—Sturm & Fix LLP

(57) ABSTRACT

A method and sling introducer (10) for installing a sub-urethral sling tape (100) through a vaginal incision wherein, the sling introducer (10) includes an instrument unit (11) having an elongated curved hollow tubular member (20) having a ported conical tip (22) and a capture aperture (21) dimensioned to receive one end of a sling tape (100) wherein, the tubular member (20) slidably receives a hollow capture piston (24) that may captively engage the sling tape (100) between the ported conical tip (22) and the capture piston (24) while saline solution is being introduced through a hollow handle member that is in open fluid communication with the hollow tubular member (20).

15 Claims, 8 Drawing Sheets

Fig. 8
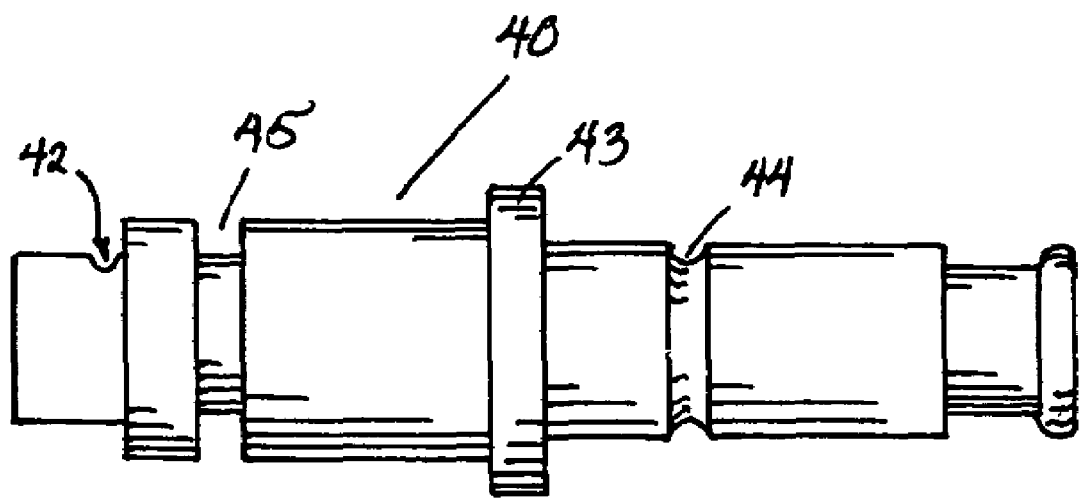
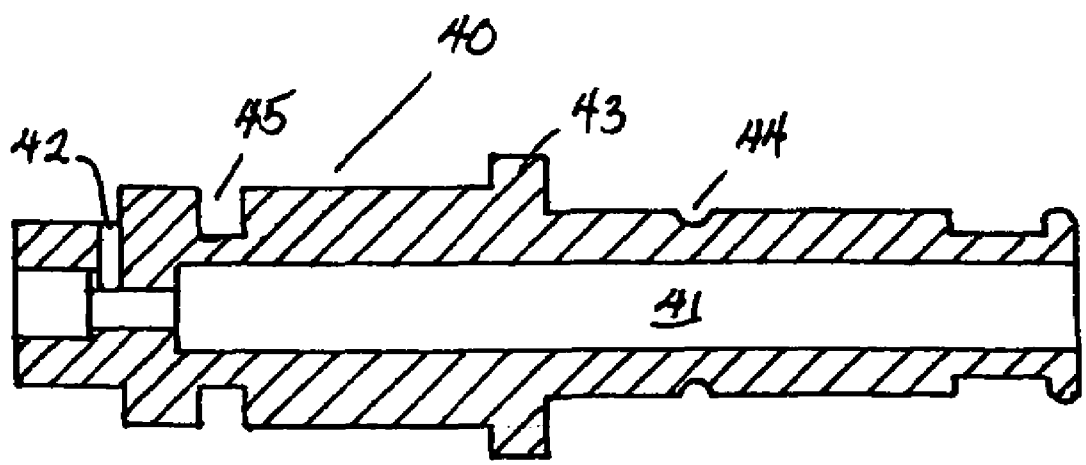
Fig. 9

URETHRAL SLING INTRODUCER AND METHOD OF USE

CROSS REFERENCE TO RELATED APPLICATIONS

Not applicable.

BACKGROUND OF THE INVENTION

1. Field of the Invention

The present invention relates to the field of medical instruments employed to control female incontinence and in particular to an apparatus for installing a sub-urethral sling and the method of installing the urethral sling.

2. Description of Related Art

As can be seen by reference to the following U.S. Pat. Nos. 6,478,727; 6,030,393; 5,899,909; 6,491,703; and 6,273,852, the prior art is replete with myriad and diverse surgical instruments employed for the sole purpose of treating female urinary incontinence.

While all of the aforementioned prior art constructions are more than adequate for the basic purpose and function for which they have been specifically designed, they are uniformly deficient with respect to their failure to provide a simple, efficient, and practical method and apparatus for installing a urethral sling in a safe and simple manner with minimal trauma to the patient's body.

All of the recent surgical procedures that have been developed to install a polypropylene sling tape in an underslung relationship to a woman's urethra for controlling incontinence require that an incision be made in the vaginal and abdominal walls which result in what is now believed to be an unnecessary surgical trauma for the patient.

In addition, the majority of surgical instruments that are currently employed in this medical procedure employ one or more curved tubular instruments wherein, the pointed tip of the curved instrument must pass between the bladder and the symphysis which requires great care and skill on the part of the surgeon.

As a consequence of the foregoing situation, there has existed a longstanding need in the medical field for a new and improved method and apparatus for installing a sub-urethral tape sling in an underslung relationship in a woman's urinary tract; and, the provision of such a method and apparatus is the stated objective of the present invention.

BRIEF SUMMARY OF THE INVENTION

Briefly stated, the urethral sling introducer that forms the basis of the present invention comprises in general an actuator handle unit, an instrument unit and a tape gauge unit wherein, the actuator handle unit operatively deploys a first captive piston moveably disposed within the instrument unit to captively grasp one end of a urethral sling tape as the instrument unit passes sequentially through a pair of incisors in the patient's vaginal wall.

As will be explained in greater detail further on in the specification, the sling tape is further slidably disposed within the tape gauge unit which comprises a transparent sheath member bearing indicia that allows the surgeon to quickly and visually determine the exact length of the portion of the sling tape that has been inserted into the first incision in the vaginal wall.

The instrument unit comprises in general a hollow curved tubular member having a ported and conical tip wherein, the interior passageway of the curved tubular member is dimensioned to receive a piston element mounted on one end of an elongated spring element the other end of which is attached to a second locking piston operatively associated with the handle unit.

In addition, the handle unit comprises a hollow handle member dimensioned to slidably receive the locking piston which has a fluid passageway that allows fluid introduced through a tubular connector element to pass through the locking piston and the curved tubular member through the capture piston and then through the ports and aperture in the conical tip to facilitate the passage of the tip between the bladder and the symphysis.

In addition, the locking piston is designed to cooperate with the handle unit such that in a first position the locking piston causes the capture piston to be retracted below a capture aperture formed in the curved tubular member; and, in a second position the captive piston will captively engage one end of the polypropylene sling tape that has been previously inserted into the capture aperture.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein:

FIG. 8 is an external view of the locking piston;

FIG. 9 is a cross-sectional view of the locking piston; and,

DETAILED DESCRIPTION OF THE INVENTION

Figure 1:
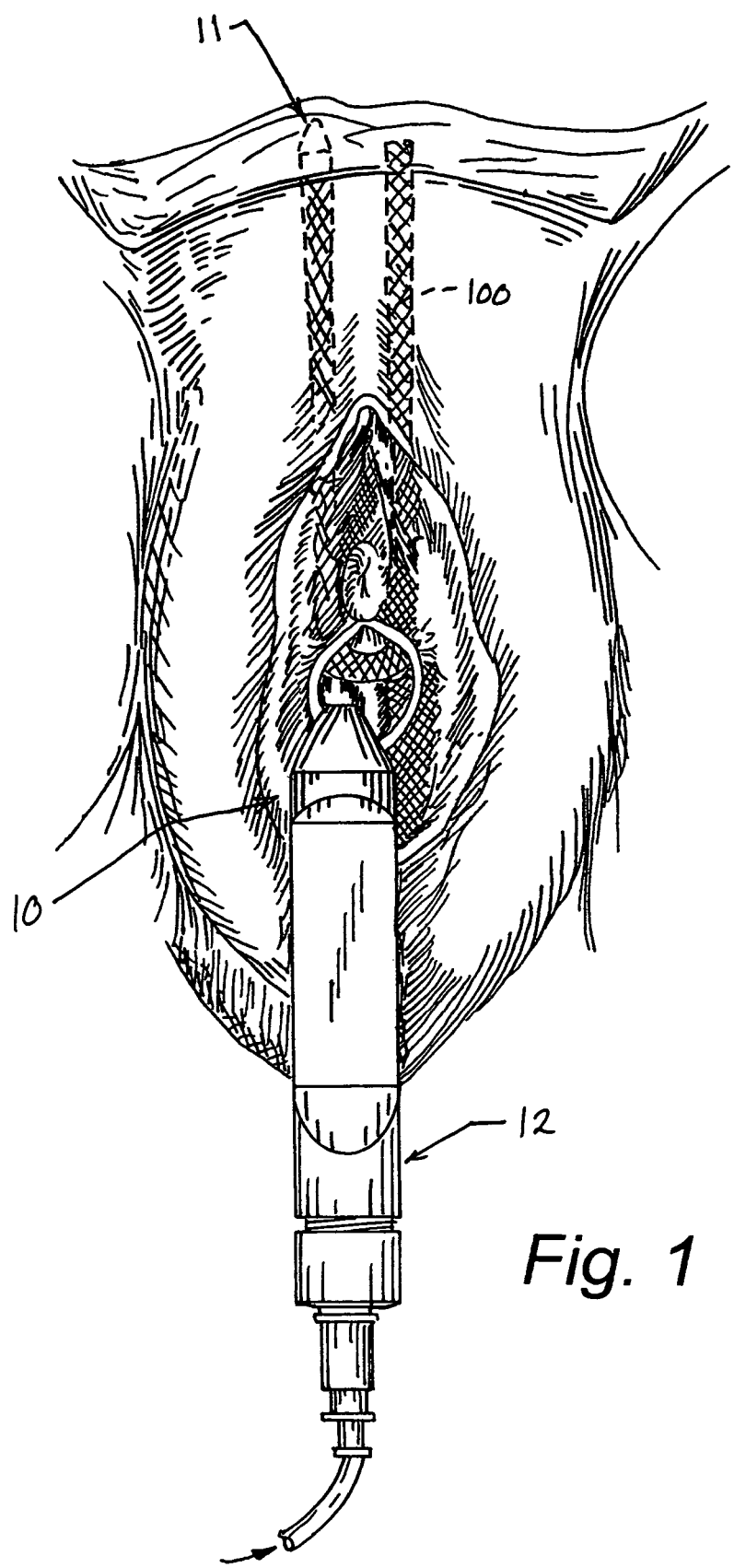
FIG. 1 shows the urethral sling introducer that forms the basis of this invention in use.

As can be seen by reference to the drawings, and in particular to FIG. 1, the urethral sling introducer that forms the basis of the present invention is designated generally by the reference number 10. The sling introducer 10 comprises in general an instrument unit 11 and a handle unit 12 that are used to operatively engage and release a polypropylene sub-urethral sling tape 100 during surgery wherein, as part of the surgical procedure, a tape gauge unit 13 is also employed to assist the surgeon in inserting equal amounts of tape through two vaginal incisions. These units will now be described in seriatim fashion.

As shown in FIGS. 2 through 5, the instrument unit 11 comprises a curved elongated hollow tubular member 20 the upper end of which is provided with a contoured capture aperture 21 and terminates in a hollow conical tip 22 provided with a plurality of fluid outlet ports 23 wherein, the purpose and function of the capture aperture 21 and the fluid outlet ports 23 will be described in greater detail further on in the specification.

Still referring to FIGS. 2 through 5, it can be seen that the interior of the elongated hollow tubular member 20 is dimensioned to slidably receive a hollow capture piston 24 the upper end of which is chamfered and the lower end of which is attached to one end of an elongated spring element 25 that extends both through the instrument unit 11 and a portion of the handle unit for reasons that will be explained presently.

Figure 2:
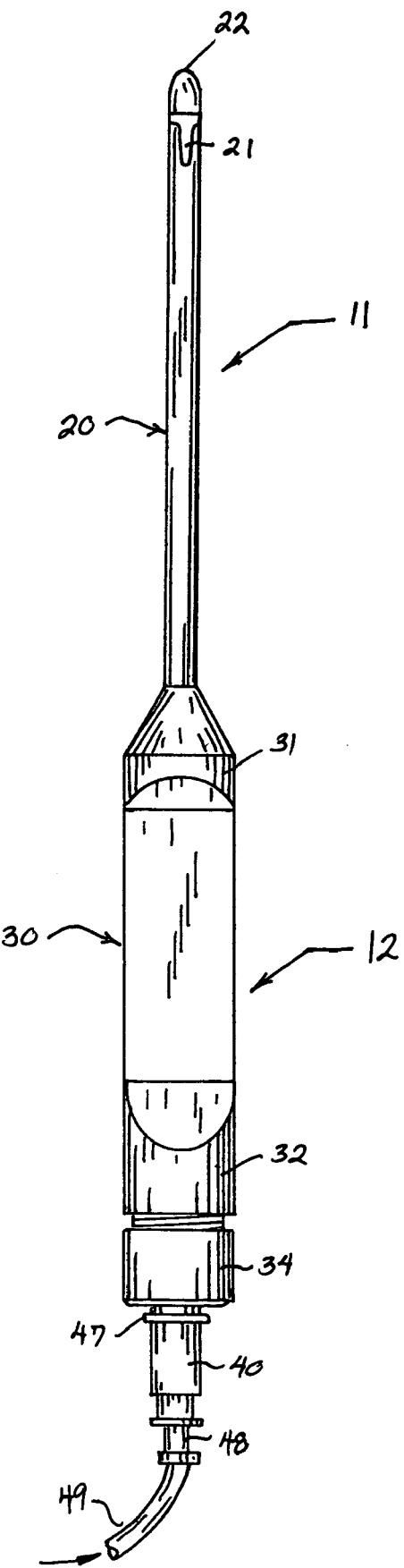
FIG. 2 is a front elevation view of the urethral sling introducer.
Figure 3:
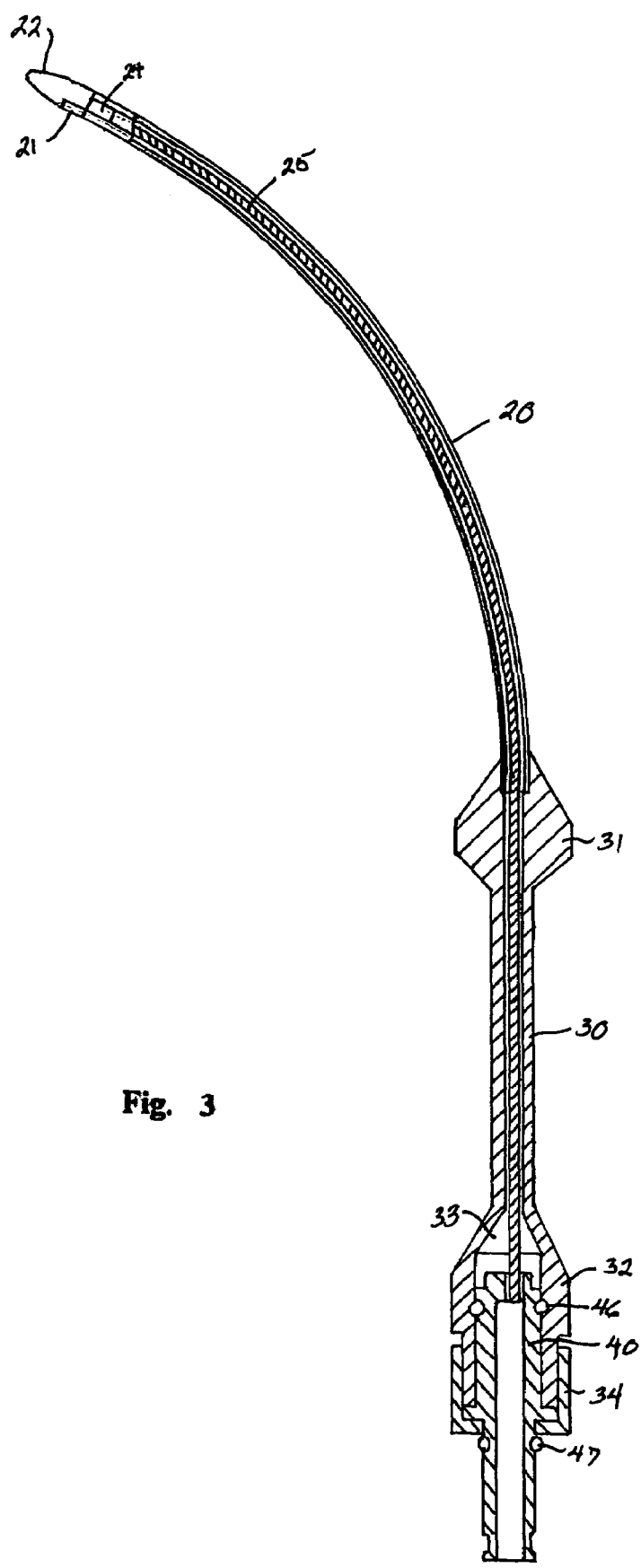
FIG. 3 is a cross-sectional view taken through line 3-3 of FIG. 2 and rotated 90°.
Figure 4:
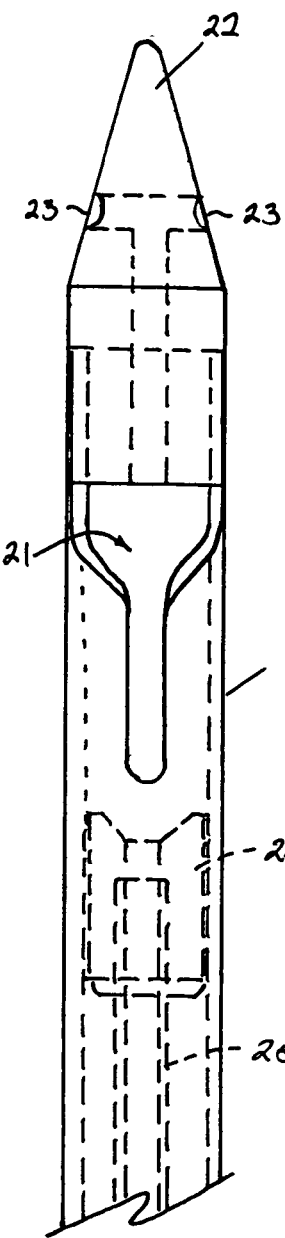
FIG. 4 is an enlarged front detail view of the upper portion of the instrument unit.
Figure 5:
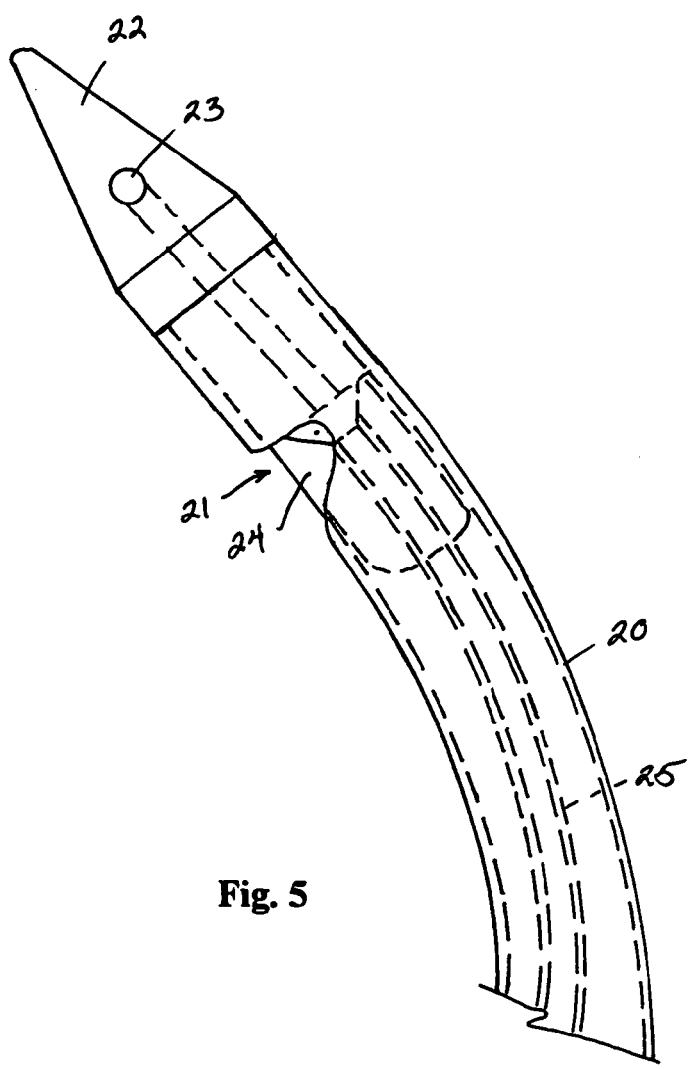
FIG. 5 is an enlarged side detail view of the upper portion of the instrument unit.

As can best be appreciated by reference to FIGS. 2 and 3, the handle unit 12 comprises an elongated hollow handle member 30 the upper and lower portions of which are provided with enlarged gripping surfaces 31 32 wherein, the upper end of the handle member 30 is fixedly secured to the lower end of the curved hollow tubular member 20 and the lower end of which defines an enlarged fluid chamber 33 dimensioned to slidably receive a locking piston 40. In addition, the lower end of the handle member 30 is adapted to receive a threaded cap element 34 to move the locking piston 40 upwardly and downwardly within the enlarged chamber 33 in the handle member 30.

Turning now to FIGS. 3, 8, and 9, it can be seen that the elongated locking piston 40 is provided with a stepped shoulder axial bore 41 and a transverse fluid port 42 disposed adjacent to but spaced from the distal end of the axial bore 41 which fixedly receives the lower end of the elongated spring element 25.

In addition, the exterior surface of the locking piston 40 is provided with an outwardly projecting collar 43 which is flanked by a pair of peripheral grooves 44 45 wherein, the collar 43 acts as a stop to limit the intrusion of the locking spool 40 into the enlarged chamber 33 of the handle member 30 and one of the grooves 45 is dimensioned to receive an O-ring 46 that is sealingly engaged with the interior walls of the enlarged chamber 33 while the other groove 44 is dimensioned to receive another O-ring 47 that will prevent the cap element from becoming disengaged with the lower end of the locking piston 40.

Furthermore, as shown in FIG. 2, the lower end of the locking piston 40 is further provided with a tube connector 48 that is adapted to receive a saline supply line such that a supply of saline fluid can be delivered through the handle unit 12 and the instrument unit 11 during the surgical procedure.

Figure 6:
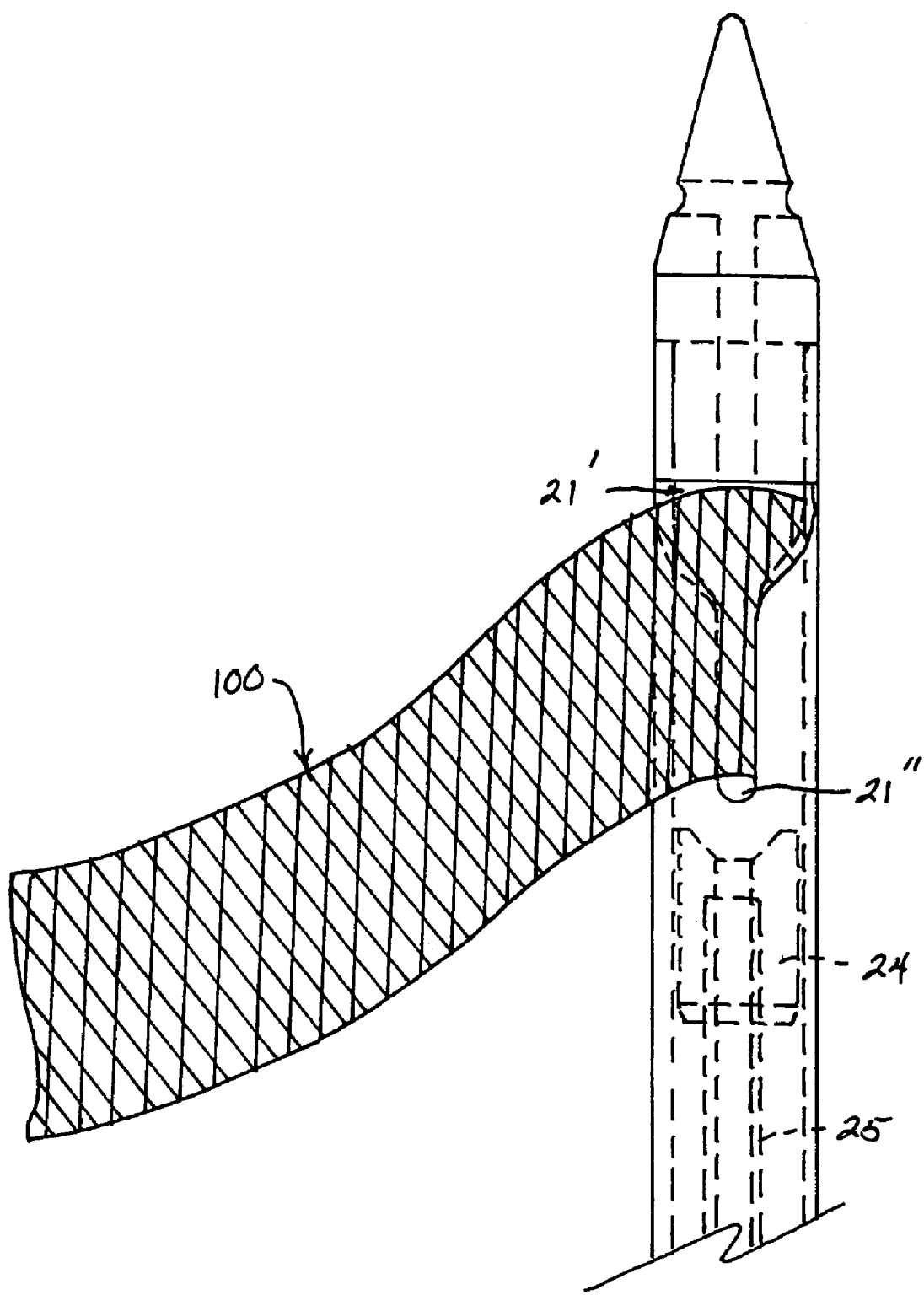
FIG. 6 is an enlarged front detail view showing the sling tape threaded through the capture aperture.
Figure 7:
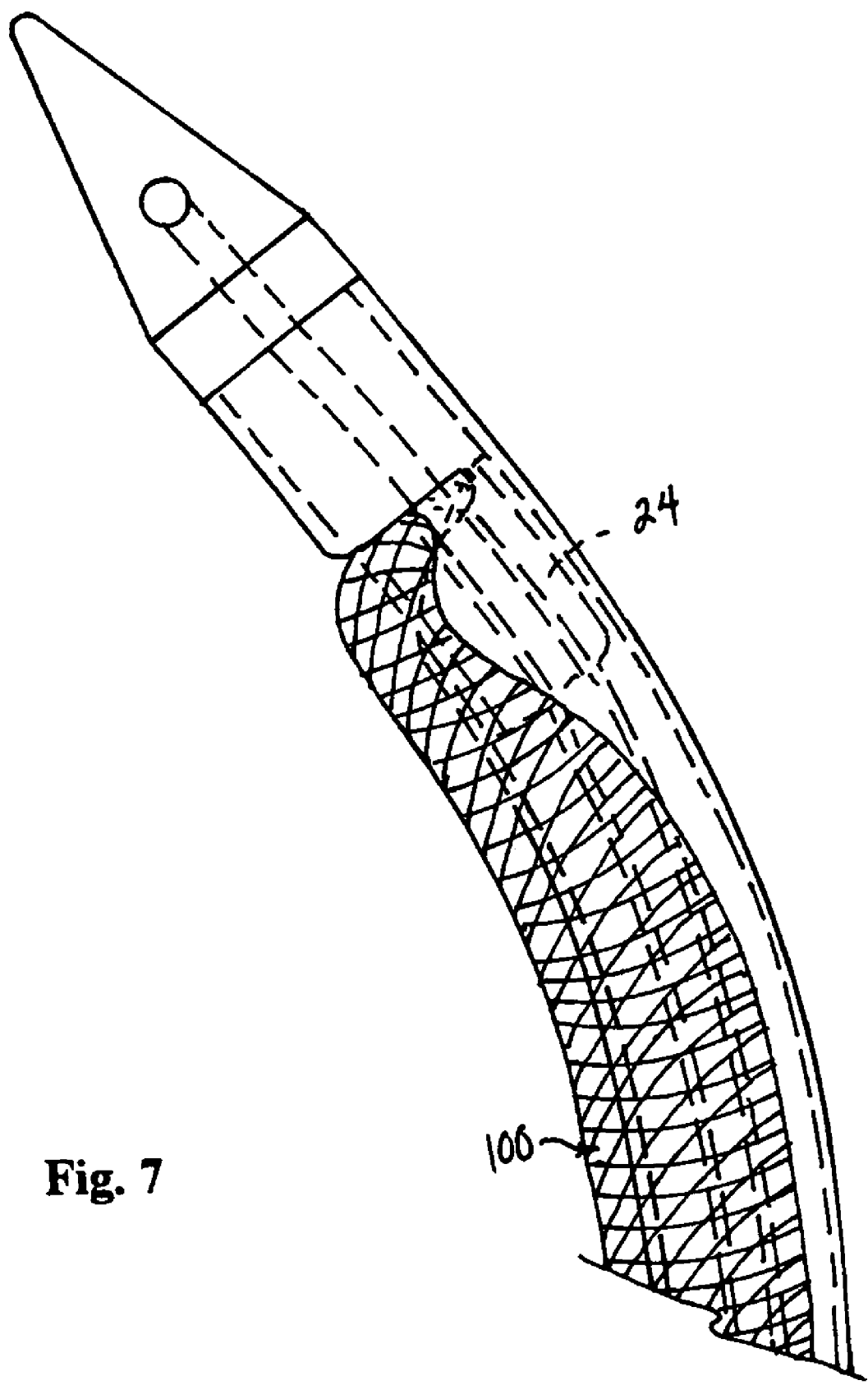
FIG. 7 is an enlarged side detail view showing the sling tape captively engaged in the capture aperture via the capture piston.

As can best be seen by reference to FIGS. 6 and 7, the contoured capture aperture 21 has an enlarged upper portion 21' and an elongated narrow lower portion 21" wherein, the lower portion 21" is dimensioned to receive the lower portion of the sling tape 100 in its uncompressed state, while the enlarged upper portion 21' of the capture aperture 21 allows the compressed bulk of the end of the sling tape 100 to be released without catching on the capture aperture 21 when the capture piston 24 is withdrawn within the hollow tubular member 20 when the conical tip 22 reaches a desired location beneath the patient's abdominal wall.

The method of use of the sling introducer 10 proceeds once a surgeon has made a pair of incisions in the vaginal wall of the patient on opposite sides of the urethral opening. Once these incisions have been made, the surgeon will back off the cap element 34 to allow the locking piston 40 to be partially withdrawn from the chamber 33 in the handle member 30.

This action causes the capture piston 24 to be withdrawn from a blocking position relative to the capture aperture 21 which can then receive one end of the sling tape 100. At this point, the capture piston is re-inserted into the chamber 33 so that the spring element 25 will force the capture piston 24 into gripping engagement with the sling tape 100 which is gripped between the bottom of the conical tip 22 and the top of the capture piston 24 whereupon the cap element 34 is advanced upwardly relative to the bottom of the handle member 30.

Once the sling tape 100 is grasped by the sling introducer 10, the surgeon will insert the conical tip 22 of the instrument unit 11 into one of the vaginal incisions using the saline solution to facilitate the passage of the conical tip between the bladder and the symphisis until such time as the presence of the conical tip 22 can be felt beneath the patient's abdominal wall.

At this juncture, the inserted end of the sling tape 100 is released by withdrawing the capture piston 24 from engagement with the sling tape and the instrument unit 11 is withdrawn from the first incision. Then in order for the surgeon to insure that equal lengths of the sling tape 100 are inserted into the pair of vaginal incisions, the tape guide unit 13 comes into play.

Figure 10:
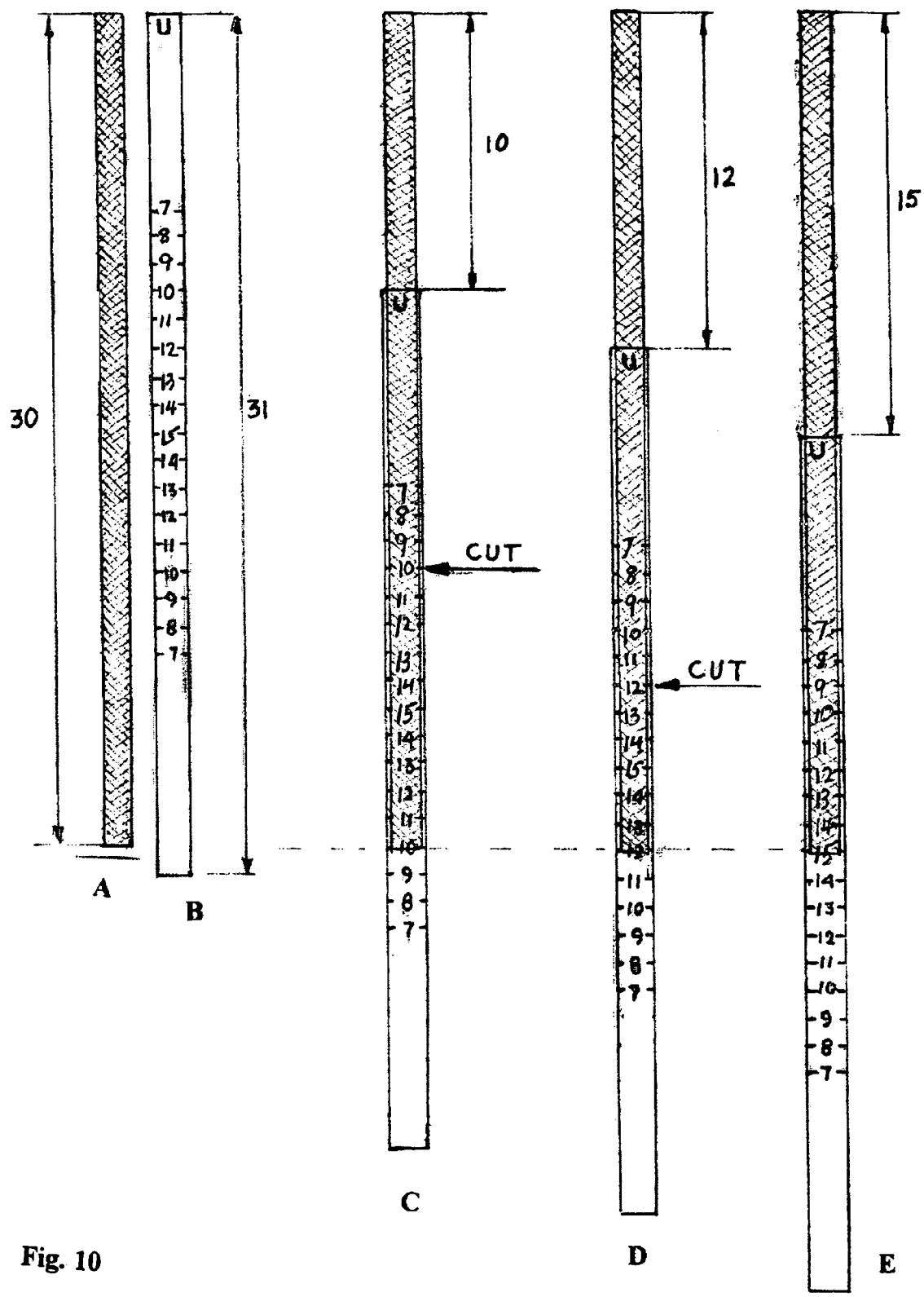
FIG. 10 is a series of sequential views illustrating the operation of the tape gauge unit.

In accordance with the teachings of this invention and as depicted in FIG. 10, the tape guide unit 13 comprises a transparent sheath member 50 that is slightly longer than, and slidably disposed on, the sling tape 100 wherein, the exterior surface of the sheath member is provided with different colored ascending/descending numerical indicia 51.

In use the sheath member 50 is snuggled against the captive end of the sling tape 100 as the sling tape 100 is inserted through the first vaginal incision by the instrument unit 11. Then once the sling tape 100 is positioned against the abdominal wall and released, the sheath member 50 is withdrawn until the top of the sheath member 50 is visible outside of the vaginal incision. At this point, the surgeon will note the position of the free end of the sling tape relative to one set of colored indicia and then sever both the sling tape 100 and the sheath 50 at the same numerical value on the different colored indicia.

In this manner, the uncut free end of the sling tape 100 can be captively engaged by the sling introducer 10 as previously described and inserted into the other vaginal incision to insure that equal lengths of sling tape 100 are installed without the necessity of creating abdominal incisions to trim the tape ends.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

Having thereby described the subject matter of the present invention, it should be apparent that many substitutions, modifications, and variations of the invention are possible in light of the above teachings. It is therefore to be understood that the invention as taught and described herein is only to be limited to the extent of the breadth and scope of the appended claims.

I claim:

1. A urethral sling introducer for inserting only through a pair of vaginal incisions equal lengths of polypropylene sling tape in a sub-urethral fashion to control female incontinence wherein, the sling introducer comprises an instrument unit including an elongated curved hollow tubular member provided with a conical tip having at least one fluid port wherein, the upper end of the hollow tubular member is provided with a contoured capture aperture and is further dimensioned to slidably receive a hollow capture piston, the capture aperture being disposed to receive an end of the sling tape;

a handle unit including a hollow handle member adapted to receive a supply of saline fluid wherein, the hollow handle member is in open communication with said hollow tubular member;

means for moving said capture piston into and out of an obstructing relationship relative to said contoured capture aperture;

wherein the capture piston has an upper end that is chamfered to allow saline fluid to pass through said capture aperture; and wherein said at least one fluid port is in open fluid communication with the hollow capture piston member.

2. The sling introducer as in claim 1; wherein, said means for moving said capture piston relative to the capture aperture comprises at least in part a locking piston slidably disposed within the hollow handle member; and an elongated spring element having opposite ends connected to said capture piston and said locking piston.

3. The sling introducer as in claim 2; wherein, said capture aperture has an enlarged upper portion and an elongated narrow lower portion.

4. The sling introducer as in claim 3; wherein, said means for moving the capture piston relative to the capture aperture further comprises a cap element movably disposed on the lower end of the handle member wherein, the cap element is disposed in a surrounding relationship relative to said locking piston.

5. The sling introducer as in claim 4; wherein, said cap element is adapted to movably engage a portion of the locking piston.

6. The sling introducer as in claim 1; wherein, said means for moving said capture piston relative tot he capture aperture comprises at least in part a locking piston slidably disposed within the hollow handle member; and an elongated spring element having opposite ends connected to said capture piston and said locking piston.

7. The sling introducer as in claim 1; wherein, said capture aperture has an enlarged upper portion and an elongated narrow lower portion.

8. The sling introducer as in claim 1; wherein, said capture aperture has an enlarged upper portion and an elongated narrow lower portion.

9. A method of installing a sub-urethral sling tape only through a pair of vaginal incisions without piercing the abdominal wall including the steps of (a) captively engaging one end of the sling tape in the upper end of an elongated hollow tubular member having a conical tip and disposed on a hollow handle member connected to a saline solution supply (b) inserting said conical tip through one of the vaginal incisions and threading the conical tip between the bladder and symphysis while introducing saline solution through the hollow tubular member (c) detecting the approach of the conical tip proximate to the abdominal wall (d) disengaging the captive end of the sling tape from the hollow tubular member; and (e) retracting the hollow tubular member from the first vaginal incision.

10. The method of claim 9; further comprising the steps of:

(f) repeating steps (a) through (e) with respect to the second vaginal incision.

11. The method as in claim 9; further including the intermediate steps of:

(g) disposing the sling tape in a transparent sheath provided with different colored numerical indicia (h) retracting the sheath slight prior to captively engaging the unsheathed portion of the sling tape as in step (a)

(i) snugging the sheath against the captive end of the tape.

12. The method as in claim 11; including the further steps of (j) retracting the transparent tape after step (c) and prior to step (d) until the upper end of the sheath passes out of the vaginal incision on the left side (k) noting the numerical value adjacent the free end of the sling tape on the lower portion of the colored indicia on the sheath (l) severing the sheath and the sling tape at the corresponding numerical value on the differently colored upper portion of the sheath; and, (m) removing the remaining portion of the sheath from the uncut portion of the sling tape.

13. The method as in claim 12; further comprising the steps of:

(f) repeating steps (a) through (e) with respect to the insertion through the incision on the right side of the urethra.

14. A urethral sling introducer for inserting only through a pair of vaginal incisions equal lengths of polypropylene sling tape in a sub-urethral fashion to control female incontinence wherein, the sling introducer comprises an instrument unit including an elongated curved hollow tubular member provided with a conical tip wherein, the upper end of the hollow tubular member is provided with a contoured capture aperture and is further dimensioned to slidably receive a capture piston a handle unit including a hollow handle member adapted to receive a supply of saline fluid wherein, the hollow handle member is in open communication with said hollow tubular member; and, means for moving said capture piston into and out of an obstructing relationship relative to said contoured capture aperture;

wherein said means for moving said capture piston relative to the capture aperture comprises at least in part a locking piston slidably disposed within the hollow handle member; and an elongated spring element having opposite ends connected to said capture piston and said locking piston.

15. A urethral sling introducer for inserting only through a pair of vaginal incisions equal lengths of polypropylene sling tape in a sub-urethral fashion to control female incontinence wherein, the sling introducer comprises an instrument unit including an elongated curved hollow tubular member provided with a conical tip wherein, the upper end of the hollow tubular member is provided with a contoured capture aperture and is further dimensioned to slidably receive a capture piston, wherein the capture aperture has an enlarged upper portion and an elongated narrow lower portion;

a handle unit including a hollow handle member adapted to receive a supply of saline fluid wherein, the hollow handle member is in open communication with said hollow tubular member; and means for moving said capture piston into and out of an obstructing relationship relative to said contoured capture aperture.

* * * * *